US012672767B2

(12) United States Patent
Wang et al.

(10) Patent No.: US 12,672,767 B2
(45) Date of Patent: Jul. 7, 2026

(54) SHIELDING DEVICE, AND MAGNETIC CONTROL CAPSULE ENDOSCOPE SYSTEM

(71) Applicant: Ankon Medical Technologies (Shanghai) Co., LTD, Shanghai (CN)

(72) Inventors: Kaifei Wang, Shanghai (CN); Xiaodong Duan, Plano, TX (US)

(73) Assignees: Ankon Medical Technologies (Shanghai) Co., LTD, Shanghai (CN); ANX IP HOLDING PTE. LTD., Singapore (SG)

( * ) Notice: Subject to any disclaimer, the term of this patent is extended or adjusted under 35 U.S.C. 154(b) by 176 days.

(21) Appl. No.: 18/833,899

(22) PCT Filed: Jan. 16, 2023

(86) PCT No.: PCT/CN2023/072312
§ 371 (c)(1),
(2) Date: Jul. 28, 2024

(87) PCT Pub. No.: WO2023/143167
PCT Pub. Date: Aug. 3, 2023

(65) Prior Publication Data
US 2025/0143555 A1 May 8, 2025

(30) Foreign Application Priority Data
Jan. 27, 2022 (CN) .......................... 202210097916.8

(51) Int. Cl.
H05K 9/00 (2006.01)
A61B 1/00 (2006.01)
(Continued)

(52) U.S. Cl.
CPC .......... *A61B 1/041* (2013.01); *A61B 1/00158* (2013.01); *A61B 1/045* (2013.01); *H05K 9/0007* (2013.01)

(58) Field of Classification Search
CPC .................................................. H05K 9/0007
See application file for complete search history.

(56) References Cited

U.S. PATENT DOCUMENTS 6,469,495 B1 * 10/2002 Boswell ............. G01R 29/0821
174/378
7,709,748 B2 * 5/2010 Hsieh ................. G01R 29/0821
174/382

(Continued)

*Primary Examiner* — Hung V Ngo
(74) *Attorney, Agent, or Firm* — Treasure IP Group , LLC

(57) ABSTRACT

The present application discloses a shielding device and a magnetic control capsule endoscope system. The shielding device is used to shield a ferromagnetic main control member supported by a support, including: a shielding case and a lifting mechanism, where the shielding case is connected to the lifting mechanism, and the lifting mechanism drives the shielding case to slide in a direction close to or away from the main control member; the shielding device further comprises a limiting structure, the limiting structure is in contact with the main control member and/or the support, used to restrict the movement of the main control member supported by the support. The present application effectively shields the magnetic field of the main control member by setting the shielding device.

11 Claims, 5 Drawing Sheets

(51) Int. Cl.
    *A61B 1/04*           (2006.01)
    *A61B 1/045*         (2006.01)

(56)                References Cited

U.S. PATENT DOCUMENTS

| | | | |
|---|---|---|---|
| 9,872,420 B1 * | 1/2018 | Sperl | E05D 3/022 |
| 2006/0289190 A1 * | 12/2006 | Mok | G01R 29/0821 |
| | | | 361/818 |
| 2010/0105984 A1 | 4/2010 | Brewer et al. | |
| 2014/0139306 A1 | 5/2014 | Chiba et al. | |
| 2015/0065801 A1 | 3/2015 | Chiba et al. | |

* cited by examiner

SHIELDING DEVICE, AND MAGNETIC CONTROL CAPSULE ENDOSCOPE SYSTEM

CROSS-REFERENCE OF RELATED APPLICATIONS

The application is a National Phase Application of PCT International Application No. PCT/CN2023/072312, International Filing Date Jan. 16, 2023, published Aug. 3, 2023 as International Publication Number WO2023/143167A1, which claims priority from Chinese Patent Application No. 202210097916.8, filed Jan. 27, 2022, all of which are incorporated herein by reference in their entirety.

FIELD OF INVENTION

The present application relates to the field of medical device technology, and more particularly to a shielding device and a magnetic control endoscope capsule system.

BACKGROUND

In the prior art, the magnetic control capsule endoscope system comprises a capsule endoscope and a magnetic control system. The movement mode, movement path, and orientation angle of the capsule endoscope may be controlled by a main control member of the magnetic control system. In specific use, the main control member of the magnetic control system is moved to its working area, or the subject enters the working area of the main control member of the magnetic control system, and then controls the capsule endoscope to move in the digestive tract in this working area to capture images of the digestive tract.

The main control member of the magnetic control system for controlling the capsule endoscope is a strong magnet made of neodymium-iron-boron (NdFeB) material. The specifications of this strong magnet are relatively large, with a surface magnetic field strength of over 850 mT, so it has a strong magnetic force on ferromagnetic items or items containing ferromagnetic parts. Based on this, when the main component is unshielded and stationary, the lack of shielding in its stationary environment may affect nearby magnetic-sensitive devices, causing the magnetic-sensitive devices to malfunction. The magnetic-sensitive devices include human implantable medical components and other electronic components. In addition, during the movement of the main component under control, due to the specific environment of the moving environment being a non-shielded magnetic field, it may affect the surrounding ferromagnetic items or equipments, and may even cause damage. In current technology, the main method is to place the magnetic control system in a separate room, thus creating a safety zone around the magnetic control system, preventing magnetic-sensitive devices from entering the safety zone, thereby ensuring the safe use of the magnetic control system.

Due to the presence of main control member with a strong magnetic field in the magnetic control system, the magnetic control system (including at least the ferromagnetic main control member) needs to be effectively shielded to prevent the main control member from causing damage to other magnetic-sensitive devices during movement and storage.

SUMMARY OF THE INVENTION

In order to solve the problem of interference to the outside world caused by the strong magnetic attraction of the ferromagnetic main control member, the present application provides a shielding device and a magnetic control capsule endoscope system, which can effectively shield the magnetic field of the main control member in the magnetic control capsule endoscope system, and provide a hardware basis for quickly switching between a working state and a shielding state of the main control member.

According to a first aspect of the present application, a shielding device is provided for shielding a ferromagnetic main control member supported by a support, comprising:

a shielding case and a lifting mechanism, where the shielding case is connected to the lifting mechanism, and the lifting mechanism drives the shielding case to slide in a direction close to or away from the main control member;

the shielding device further comprises a limiting structure, where the limiting structure is in contact with the main control member and/or the support, for restricting the movement of the main control member supported by the support.

Optionally, the lifting mechanism comprises:

a sliding support member;

a sliding assembly, where the sliding assembly is fixedly connected to the shielding case and sliding along the sliding support member to drive the shielding case away from the main control member or enclose the main control member; and, a lifter, and a push rod for controlling the lifting and lowering of the shielding case by the lifter, where the push rod is connected to the shielding case to drive the shielding case to slide in the direction close to or away from the main control member.

Optionally, the limiting structure comprises a supporting structure and a limiting member, where the limiting member is disposed at one end of the supporting structure near the main control member, and the limiting member is in contact with the main control member and/or the support under the support of the supporting structure, and restricts the movement of the main control member.

Optionally, the support is configured as a robotic arm, the supporting structure comprises a support frame, and the limiting member comprises a clamping member;

the support frame is used to support the clamping member;

the clamping member is fixed to the top of the support frame, and the clamping member is used to clamp the robotic arm to restrict the movement of the main control member.

Optionally, the robotic arm comprises a first sub-arm and a second sub-arm rotatably connected, and the clamping member is configured as a groove;

the groove is used to embed the second sub-arm, and when the second sub-arm is embedded in the groove, the projections of the first sub-arm and the second sub-arm on the target plane are two straight lines with a fixed angle, where the target plane is the plane where the bottom of the groove is located;

and, during the rotation of the first sub-arm, only one position in which the second sub-arm can be embedded into the groove.

Optionally, the limiting structure further comprises a groove lifter, which is used to control the lifting and lowering of the support frame so that the clamping member may be raised and lowered by the groove lifter and the support frame.

Optionally, the supporting structure comprises a supporting platform, the shielding case is arranged on the outside of the supporting platform, and the sliding support member is arranged on one side of the supporting platform;

the supporting platform comprises a fixing frame and a supporting plate, where the supporting plate is installed through the fixing frame, and the supporting plate is used to support the main control member;

the limiting member is disposed on the edge of the side of the supporting plate facing the main control member to restrict the movement of the main control member.

Optionally, the limiting member comprises a protective sliding plate, which is disposed at the edge of the surface of the supporting plate, and the side of the protective sliding plate facing the shielding case in an upright state is a smooth surface.

Optionally, a sliding plate groove is provided on the surface of the supporting plate;

the protective sliding plate is installed in the groove of the sliding plate groove in a manner that rotates around its bottom, where the protective sliding plate is disposed upright in the sliding plate groove in a magnetic shielding state, and embedded in the sliding plate groove in a non-magnetic shielding state;

the supporting platform further comprises a locking structure, the locking structure comprising a locking button, and the locking structure is used to control the protective sliding plate in a locked state or an unlocked state in the sliding plate groove through the locking button.

Optionally, the main control member comprises a magnet, where the magnet is enclosed through the main control member shell;

the limiting member comprises a bearing table, where the bearing table is fixed on the surface of the supporting platform for bearing the main control member;

the tabletop of the bearing table and the end of the main control member shell near the bearing table are shaped to be embedded in each other.

According to a second aspect of the present application, a magnetic control capsule endoscope system is provided, comprising:

the above-mentioned shielding device, the ferromagnetic main control member, and the support for supporting the main control member, and a fixture platform for installing the support;

where the support supports the main control member for movement, and the shielding case of the shielding device is used to shield the main control member supported by the support.

The shielding device provided in the present application comprises a shielding case, a sliding support member, a sliding assembly, a lifter, and a push rod that controls the lifting and lowering of the shielding case through the lifter. The sliding support member, the sliding assembly, the lifter, and the push rod together form a lifting mechanism that drives the lifting and lowering of the shielding case. Therefore, the shielding case may be positioned around or away from the main control member, providing a hardware basis for the switching operation of the main control member between the working state and the shielding state. When the shielding case is arranged around the main control member by lifting, it can shield the strong magnetic field of the main control member and achieve the purpose of effectively shielding strong and static magnetic fields. In addition, the present application uses a limiting structure to support and restrict the movement of the main control member, preventing contact between the main control member and the shielding case, thereby ensuring the shielding effect.

BRIEF DESCRIPTION OF THE DRAWINGS

The above and other objects, features and advantages of the present application shall be made clearer by the following description of embodiments of the present application with reference to the accompanying drawings.

DETAILED DESCRIPTION

Figure 1:
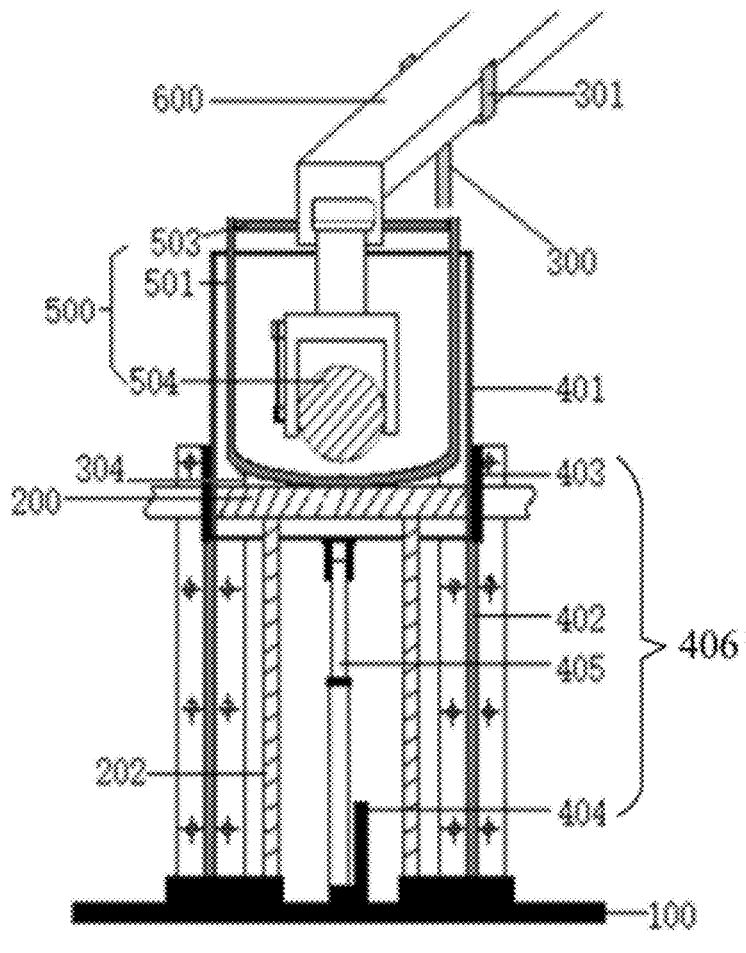
FIG. 1 shows a schematic cross-sectional view of a shielding device according to the present application.

The present application will be described in more detail below with reference to the accompanying drawings. In the various accompanying drawings, the same elements are represented by similar reference numerals. For clarity, the various parts of the accompanying drawings are not drawn to scale. In addition, some well-known parts may not be shown in the drawings.

Many specific details of the present application are described below, such as the structure, materials, dimensions, processing techniques, and techniques, of the devices, in order to understand the present application more clearly. However, as may be understood by those skilled in the art, the present application may be implemented without following these particular details.

FIG. 1 shows a schematic cross-sectional view of a shielding device according to a first embodiment of the present application. Referring to FIG. 1, the shielding device is installed on a fixture platform 100 to shield the ferromagnetic main control member 500 supported by a support 600. The shielding device comprises a shielding case 401 and a lifting mechanism 406, wherein the lifting mechanism 406 drives the shielding case 401 to slide in a direction close to or away from the main control member 500. Specifically, the lifting mechanism 406 comprises: a sliding support member 402, a sliding assembly 403, a lifter 404, and a push rod 405 for controlling the lifting and lowering through the lifter 404. The sliding support member 402 is fixed on the fixture platform 100. The sliding assembly 403 is fixedly connected to the outer side wall of the shielding case 401 and slide along the sliding support member 402 to drive the shielding case 401 away from the main control member 500 or enclose the main control member 500. The top of the push rod 405 is connected to the shielding case 401 (for example, the top of the push rod 405 is connected to the wall of the shielding case 401) to drive the shielding case 401 to slide in the direction close to or away from the main control member 500.

Specifically, the above-mentioned fixture platform 100 may use a movable structure, that is, the fixture platform 100 can move. The above fixture platform 100 may also use a fixed structure, that is, the fixture platform 100 is fixed on the ground. For the fixed fixture platform 100, it may be replaced by the ground for example.

The sliding support member 402 may be a guide rail, and the sliding assembly 403 may be a slider. In this case, with reference to FIG. 2 and FIG. 3, the guide rail may comprise a guide rail support 4021 and a fixed guide rail 4022, wherein the guide rail support 4021 may be plate-shaped and vertically fixed on the fixture platform 100, and the fixed guide rail 4022 is fixed on the guide rail support 4021 with screws and protrudes to be attached to the guide rail support 4021, and the fixed guide rail 4022 extends parallel to the axial direction of the shielding case 401. The slider is provided with a sliding groove embedded with the fixed guide rail 4022, so as to slide along the fixed guide rail 4022. In other embodiments, the sliding groove may be disposed on the fixed guide rail 4022, and the sliding assembly 403 is disposed within the sliding groove to drive the shielding case 401 to move along the fixed guide rail 4022.

The main control member 500, as shown in FIG. 1, may be constructed by enclosing a magnet 504 through a main control member shell 501, the main control member shell 501 playing a protective role for the magnet 504. Additionally, the main control member shell 501 may be fixed on the support 600 through rigid connecting elements such as a cross beam 503, while the movement of the magnet 504 itself is controlled by the a motor assembly (such as including a horizontal rotation motor and a vertical rotation motor, etc.). Here, the magnet 504 may be made of a magnetic material such as neodymium magnet, and the shape of magnet 504 may be spherical, etc. It should be emphasized that the present application does not limit the specific shape of the magnet 504, as long as it can achieve the control of the capsule endoscope.

The shielding case 401 may be in a cylindrical shape, and the shielding case 401 may be formed as a multi-layer structure. Preferably, the shielding case 401 may be a single-layer cylindrical shape, with a length-to-diameter ratio of 1:1 to 1.1:1, in order to save space, make installation relatively simple, and meet the miniaturization and mobility requirements of equipment. In other embodiments, the shielding case 401 may also be in the shape of a top-open barrel or a top-open hemisphere, or other shapes that can shield static magnetic fields, which may not be described here.

It should be noted that the main control member 500 moves with the support of the support 600 as the support 600 moves. When the support 600 stops moving, the main control member 500 remains relatively stationary and the shielding case 401 surrounds the main control member 500, the strong magnetic field of the main control member 500 is shielded by the shielding case 401, and the main control member 500 is in a magnetic shielding state. When the shielding case 401 is removed from around the main control member 500, the main control member 500 is in a non-shielding state. In this situation, the strong magnetic field of the main control member 500 may be used to control the movement of the capsule endoscope, so the main control member 500 may also be referred to as being in a working state. For the main control member 500 in a relatively static state, the magnetic field of the main control member 500 is a static magnetic field. The shielding principle of the shielding case 401 for shielding the relatively strong static magnetic field around the main control member 500 is: to use materials with low coercive force, high magnetic permeability, and high saturation magnetic induction intensity to surround the main control member 500, to establish a magnetic field path around the main control member 500, thereby achieving the magnetic field shielding effect.

In the embodiments of present application, the sliding support member 402 and the sliding assembly 403 form a sliding support part, and the lifter 404 and the push rod 405 form a sliding assist part. These two major parts constitute the lifting mechanism 406 for driving the lifting of the shielding case 401. The shielding case 401 can slide smoothly and conveniently in the vertical direction under the drive of the lifting mechanism 406. When the shielding case 401 is arranged around the main control member 500 by lifting, the strong magnetic field of the main control member 500 can be shielded, so as to achieve the purpose of effectively shielding the strong and static magnetic fields. Meanwhile, the lifting mechanism 406 enables the main control member 500 to flexibly switch between the shielding state and the non-shielding state, providing a hardware basis for the switching operation of the main control member 500 between the working state and the shielding state in automated control.

Due to the heavy weight of the main control member 500 suspended on the support 600, and the relatively long movement process of entering the shielding case 401, even slight shaking may cause the main control member 500 to easily come into contact with the shielding case 401, affecting the magnetic shielding effect. Therefore, the shielding device in the present application needs to restrict the movement of the main control member 500. In an optional embodiment, the shielding device further comprises a limiting structure 300, which is used to restrict the movement of the main control member 500 supported by the support 600, thereby ensuring that the main control member 500 can remain in a stationary state without being affected (such as reducing the influence of the attraction of the shielding case 401 on the main control member 500, etc.). Specifically, the limiting structure 300 comprises a supporting structure and a limiting member. The limiting member is disposed at one end of the supporting structure near the main control member 500. The limiting member is in contact with the main control member 500 and/or the support 600 under the support of the supporting structure, restricting the movement of the main control member 500 to prevent contact between the main control member 500 and the shielding case 401.

The optional structures of the limiting structure 300 are detailed below:

(1) A First Optional Structure of the Limiting Structure 300

Figure 2:
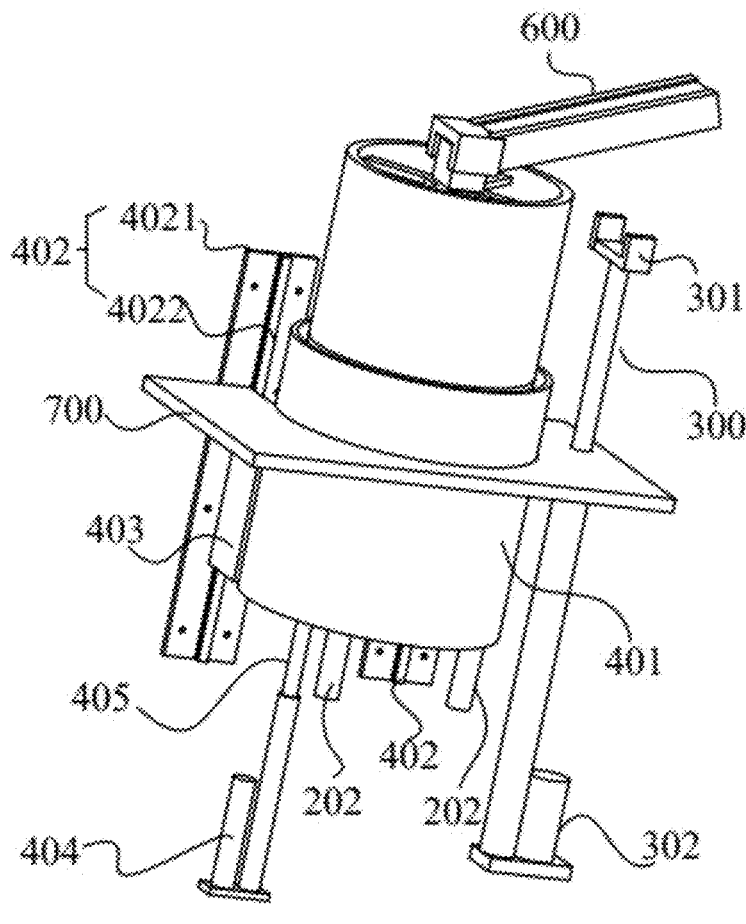
FIG. 2 shows a structural schematic diagram of a structure of the shielding device according to the present application.
Figure 3:
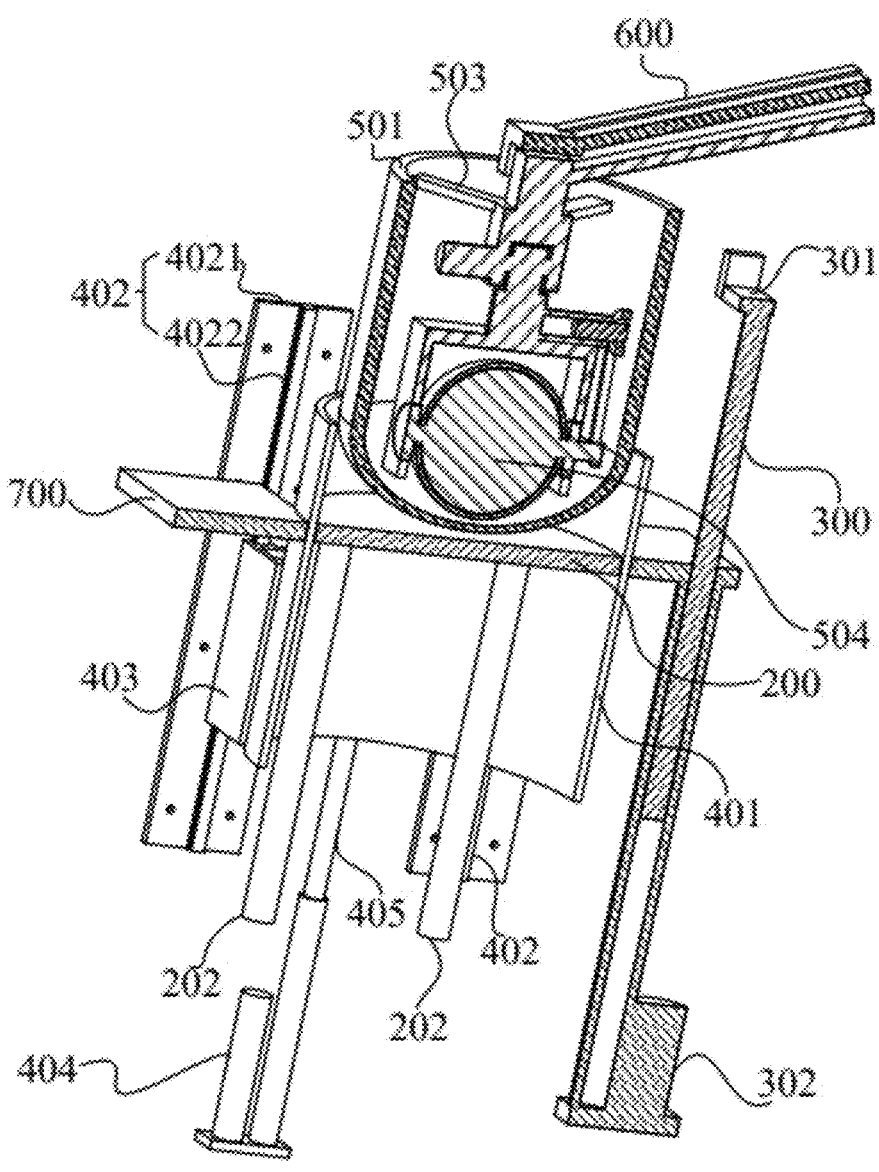
FIG. 3 shows a schematic cross-sectional view of the shielding device as shown in FIG. 2 along the central axis of the bottom surface of the clamping member groove.

As shown in conjunction with FIG. 1, FIG. 2, and FIG. 3, the support 600 is a robotic arm, and the limiting structure 300 comprises a supporting structure and a limiting member. The limiting member comprises a clamping member 301, and the supporting structure comprises a support frame for supporting the clamping member 301. The clamping member 301 is fixed to the top of the support frame, and the clamping member 301 is used to clamp the robotic arm to restrict the movement of the main control member 500.

It should be noted that, after fixing the height and angle of the clamping member 301, the clamping member 301 is mainly used to restrict the movement of the main control member 500 on a plane parallel to the surface of the fixture platform 100. In addition, the clamping member 301 can also prevent the main control member 500 from lowering, that is, the clamping member 301 also supports the main control member 500 and restricts the lowering of the main control member 500. Therefore, the clamping part 301 overall plays a reinforcing role for the stationary state of the main control member 500.

Further, the limiting structure 300 also comprises a groove lifter 302. The support frame may be connected to the groove lifter 302 at the bottom to control the lifting and lowering through the groove lifter 302. Thus, the clamping member 301 may be raised and lowered with the help of the groove lifter 302 and the support frame, so that the clamping member 301 can cope with different heights of the main control member 500 and support the main control member 500. In other words, the clamping member 301 may be combined with the robotic arm as much as possible to ensure that the main control member 500 is not affected by the shielding case 401 and remains in the stationary state.

Figure 4:
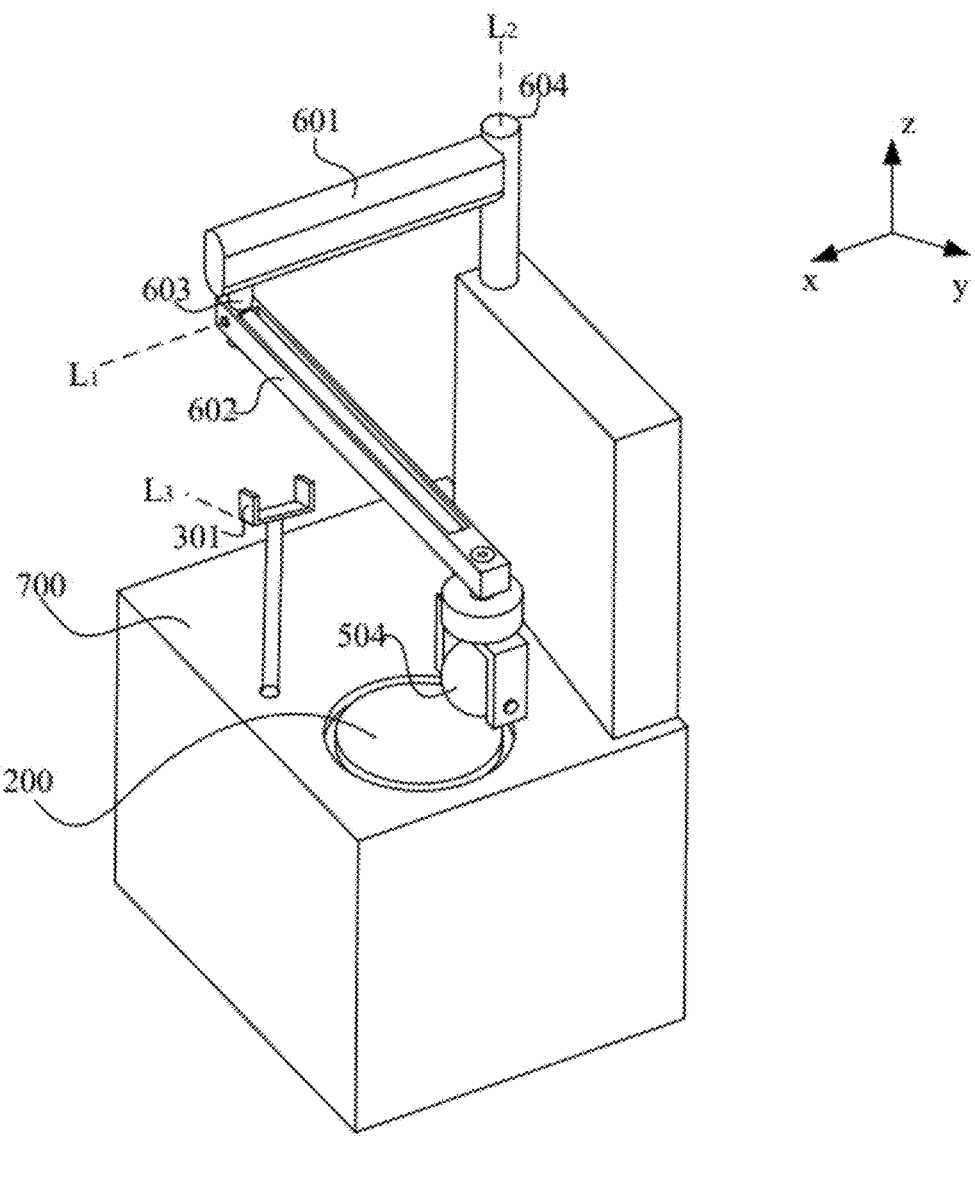
FIG. 4 shows a schematic diagram of the structure of a robotic arm according to the present application.

Referring to FIG. 4, the robotic arm may specifically comprise a first sub-arm 601 and a second sub-arm 602 rotatably connected to each other, and the clamping member 301 is configured as a groove, wherein the groove is used to embed the second sub-arm 602, and when the second sub-arm 602 is embedded in the groove, the projections of the first sub-arm 601 and the second sub-arm 602 on the target plane are two straight lines with a fixed angle, and the target plane is the plane where the bottom of the groove is located; and during the rotation of the first sub-arm 601, there is only one position in which the second sub-arm 602 can be embedded in the groove.

Optionally, the robotic arm further comprises an intermediate joint 603 disposed between the end of the first sub-arm 601 and the beginning of the second sub-arm 602, and a starting joint 604 disposed at the beginning of the first sub-arm 601. The starting joint 604 is used to rotate the first sub-arm 601 to achieve the relative rotation of the entire robotic arm, and the intermediate joint 603 is used to achieve the rotation of the first sub-arm 601 relative to the second sub-arm 602.

For example, as shown in FIG. 4, with the target plane being the xy plane, the second sub-arm 602 rotates around axis L1 (axis L1 along the x-axis direction), then the projections of the first sub-arm 601 and the second sub-arm 602 on the target plane are two straight lines with a fixed angle. Accordingly, if the groove arm of the groove of the clamping member 301 is disposed along the axis L3 (axis L3 along the y-axis direction), and the first sub-arm 601 rotates around the axis L2 (axis L2 along the z-axis direction), then during the process of the first sub-arm 601 rotating to drive the second sub-arm 602 to rotate, there is only one position where the second sub-arm 602 is parallel to the y-axis, and at this position the second sub-arm 602 may be embedded in the groove. Additionally, the first sub-arm 601 rotates around the axis L2, so that the first sub-arm 601 controls the orientation of the magnet 504 in the xy plane. The second sub-arm 602 rotates around the axis L1, causing the end of the second sub-arm 602 close to the magnet 504 to rotate up and down, thereby controlling the height of the magnet 504 along the z-axis direction.

In the embodiment of the present application, the above orientation relationship between the groove and the robotic arm effectively prevents the movement of the robotic arm joint due to the gravitational force of the magnet 504 on the shielding case 401. Further, the above orientation relationship between the groove and the robotic arm, combined with the height-adjustable groove, can more effectively restrict the movement of the robotic arm caused by the magnetic attraction of the shielding case 401 to the magnet 504, thereby further ensuring the continuous maintenance of the stationary state of the main control member 500. In addition, the groove can also prevent the impact of equipment shaking on the main control member 500, further preventing contact between the main control member 500 and the shielding case 401.

In other embodiments of the present application, the main control member 500 achieves suspension under the clamping of two or more robotic arms. These robotic arms include, for example, a driving arm and a balancing arm, etc., but the working principle of the shielding device is the same, and will not be elaborated here.

(2) A Second Optional Structure of the Limiting Structure 300

Figure 5:
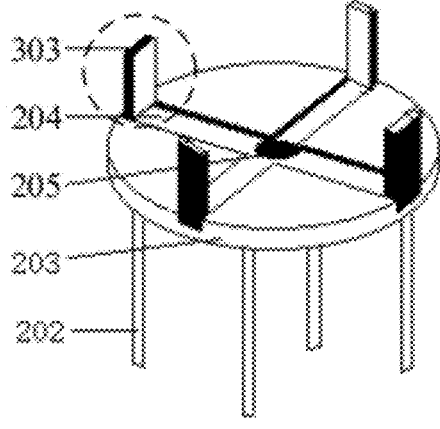
FIG. 5 shows a schematic diagram of one structure of a supporting platform according to the present application.

As shown in FIG. 3, the limiting structure 300 comprises a supporting structure and a limiting member. The supporting structure comprises a supporting platform 200. The supporting platform 200 is used to support the main control member 500, the shielding case 401 is arranged on the outside of the supporting platform 200, and the sliding support member 402 is arranged on one side of the supporting platform 200. In this situation, if the shielding case 401 slides below the surface of the supporting platform 200, it moves away from the main control member 500; if the shielding case 401 slides above the surface of the supporting platform 200, it surrounds the main control member 500. As shown in FIG. 5, the supporting platform 200 comprises a supporting plate 203 and a fixing frame 202 for setting the supporting plate 203 on the fixture platform 100. Here, the supporting plate 203 provides the tabletop of the supporting platform 200, and the supporting plate 203 is used to support the main control member 500. The limiting member is disposed on the edge of the side of the supporting plate 203 facing the main control member 500 to restrict the movement of the main control member 500.

It should be noted that, in the embodiments of the present application, the tabletop of the supporting platform 200 is the end face of the side of the supporting platform 200 facing the main control member 500. The method of installing the supporting platform 200 on the fixture platform 100 may be diverse, such as through threaded fit, mortise and tenon fit, and riveting fit, etc., as long as it can ensure the connection strength between the two.

Optionally, as shown in FIG. 4, in order to facilitate the operation of the operator, the shielding device also comprises an operating platform 700, which is disposed around the supporting platform 200. Tools that may be used by the operator may be placed on the operating platform 700.

Specifically, with reference to FIG. 5, the fixing frame 202 and the supporting plate 203 can form a "round table" structure, that is, the fixing frame 202 is composed of four table legs, and the supporting plate 203 is circular and supported by four table legs.

Figure 6:
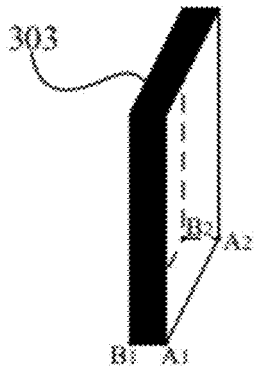
FIG. 6 shows a schematic diagram of the structure of the protective sliding plate circled in FIG. 5.

Further, as shown in FIG. 6, the limiting member comprises a protective sliding plate 303, which is disposed at the edge of the surface of the supporting plate 203 (the side facing the main control member 500), and the protective sliding plate 303, when in an upright state, the side facing the shielding case 401 (the side shaded in black in FIG. 5) is a smooth surface. Therefore, the protective sliding plate 303 confines the main control member 500 to the supporting plate 203, while also separating the main control member 500 and the shielding case 401 sliding around the supporting plate 203, and the protective sliding plate 303 provides good sliding guidance for the shielding case 401. It should be noted that the shielding case 401 is disposed on the outer side of the edge of the supporting platform 200, and the shielding case 401 is placed below the supporting plate 203 or above the supporting plate 203 by sliding. It should be understood that when the shielding case 401 is placed below the supporting plate 203, the main control member 500 is in the non-shielding state; if the shielding case 401 is placed above the supporting plate 203, the main control member 500 is in the shielding state.

In an optional embodiment, as shown in FIG. 5, a sliding plate groove 204 is provided on the surface of the supporting plate 203, and the protective sliding plate 303 is installed in the groove of the sliding plate groove 204 in a manner that rotates around its bottom. Wherein, the protective sliding plate 303 is disposed upright in the sliding plate groove 204 when the main control member 500 is in the magnetic shielding state, and is embedded within the sliding plate groove 204 when the main control member 500 is in the non-magnetic shielding state.

In order to switch the state of the protective sliding plate 303, the supporting platform 200 also comprises a locking structure (not shown), the locking structure comprises a locking button 205, the locking structure is used to control the protective sliding plate 303 to be in a locked state or an unlocked state within the sliding plate groove 204 through the locking button 205.

It should be noted that the protective sliding plate 303 is in a locked state in the sliding plate groove 204, that is, the protective sliding plate 303 is in an upright state in the sliding plate groove 204, which corresponds to the magnetic shielding state of the main control member 500. The protective sliding plate 303 is in an unlocked state in the sliding plate groove 204, that is, the protective sliding plate 303 is in an embedded state (lying down) in the sliding plate groove 204, which corresponds to the non-magnetic shielding state of the main control member 500.

Specifically, a plurality of the protective sliding plates 303 may be provided, and the protective sliding plates 303 may be disposed around the center of the supporting plate 203 and near the edge of the supporting plate 203, so as to provide a better limiting effect on the main control member 500 by surrounding it and forming a gap between the main control member 500 and the shielding case 401, and provide a better guiding sliding effect on the shielding case 401. It should be emphasized that the present application does not specifically limit the number and configuration of the plurality of the protective sliding plates 303. As long as the protective sliding plate 303 can achieve relative movement or rotation with respect to the supporting plate 203 and ensure the implementation of limiting function and guiding sliding function, it is acceptable.

Preferably, the protective sliding plates 303 are evenly spaced on the supporting plate 203. For example, if there are four protective sliding plates 303 as shown in FIG. 5, these four protective sliding plates 303 may be arranged at the groove end of the "Cross" type sliding plate groove as shown in FIG. 5; if there are three protective sliding plates 303, these three protective sliding plates 303 may be arranged at the groove end of the "Y" type sliding plate groove; if there are eight protective sliding plates 303, these eight protective sliding plates 303 may be arranged at the groove end of the "Star" type sliding plate groove. The protective sliding plates 303 are disposed at the groove end of the sliding plate groove, that is, the protective sliding plates 303 are disposed near the edge of the supporting plate 203.

As shown in conjunction with FIG. 1, FIG. 2, and FIG. 3, in the above main control member 500, the magnet 504 is a magnetic ball, the main control member shell 501 is at least partially cylindrical, and the height of the protective sliding plate 303 may be the radius of the magnetic ball as the lower limit. In addition, during the process of the protective sliding plate 303 rotating around its bottom, the maximum angle between it and the surface of the supporting plate 203 is set in the range of 90° to 95°. Within this range, the protective sliding plate 303 can not only effectively isolate the inner wall of the shielding case 401 from the main control member shell 501, but also prevent direct contact between the inner wall of the shielding case 401 and the main control member shell 501. Further, the protective sliding plate 303 results in a gap between the shielding case 401 and the main control member 500, which allows the shielding case 401 to resist the attraction of magnet 504 and slide smoothly.

The above-mentioned locking structure can specifically use existing structures. For example, the sliding plate groove 204 and the protective sliding plate 303 are shown in FIG. 5 and FIG. 6 (that is, the protective sliding plate 303 is rectangular in shape, and there are four protective sliding plates 303 which are respectively disposed at the groove ends of the "Cross" type sliding plate groove, each protective sliding plate 303 rotating around the axis A1A2 on the inner bottom), the locking structure comprises springs and the above-mentioned locking button 205, and the two opposite protective sliding plates 303 on the sliding plate groove 204 are connected to each other through springs connected between the outer axis B1B2. In this way, when the two opposite protective sliding plates 303 are embedded in the sliding plate groove 204, the spring is in a naturally stretched state, so the protective sliding plate 303 may be locked in this state when embedded in the sliding plate groove 204; however, when the locking button 205 is pressed, the locking button 205 presses on the spring and elongates it, the restoring force of the spring pulls the two connected protective sliding plates 303, causing these two protective sliding plates 303 to spring up to an upright position.

It is worth mentioning that, in other implementations, one end of the protective sliding plate 303 that docks with the sliding plate groove 204 is formed with a rounded corner or formed into an arc surface, allowing the protective sliding plate 203 to rotate flexibly within the sliding plate groove 204. More preferably, taking the example of the protective sliding plate 203 when embedded (lying) in the sliding plate groove 204, the end of the protective sliding plate 203 in contact with the sliding plate groove 204 is formed as a right angle on the side near the surface of the supporting platform 200, and as a rounded corner or an arc surface on the side near the bottom of the sliding plate groove 204.

In the embodiments of the present application, the setting of the sliding plate groove 204 and the locking structure enables the protective sliding plate 303 to flexibly switch between the locked state and the unlocked state based on whether the main control member 500 is in a shielding state. This provides a hardware basis for the flexible switching between the locked state and the unlocked state, which is beneficial for maintaining consistency between the setting state of the protective sliding plate 303 and the switching of the state of the main control member 500.

(3) A Third Optional Structure of Limiting Structure 300.

As shown in FIG. 1, the limiting structure 300 comprises a supporting structure and a limiting member. The supporting structure comprises a supporting platform 200, the shielding case 401 is disposed outside the supporting platform 200, and the sliding support member 402 is disposed on one side of the supporting platform 200. In this situation, if the shielding case 401 slides below the surface of the supporting platform 200, it moves away from the main control member 500; if the shielding case 401 slides above the surface of the supporting platform 200, it surrounds the main control member 500. The limiting member comprises a bearing table 304, the bearing table 304 is fixed on the surface of the supporting platform 200 for bearing the control main member 500. The main control member 500 comprises a magnet 504, which is enclosed by the main control member shell 501. The tabletop of the bearing table 304 (the side facing the main control member shell 501) and the end of the main control member shell 501 near the bearing table 304 are shaped to be embedded in each other. The bearing table 304 hinders the movement of the main control member shell 501, thus allowing the main control member 500 to be stably supported on the bearing table 304.

Specifically, the bottom of the main control member shell 501 may be selected as hemispherical, and the tabletop of the bearing table 304 may also be selected as hemispherical, so that the bottom of the main control member shell 501 may be embedded in the tabletop of the bearing table 304.

It should be noted that the tabletop of the bearing table 304 may be either a continuous structure or a non-continuous structure, as long as it is in a mutually embedded shape with the bottom surface of the main control member shell 501. For example, if the bottom of the main control member shell 501 is hemispherical, the tabletop of the bearing table 304 may be hemispherical with hollowed-out parts, etc.

For the shielding device, any of the optional structures of the limiting structure 300 may be selected under the conditions allowed by the actual situation. Further, the various optional structures for the limiting structure 300 may be combined for use under conditions allowed by the actual situation, such as combining the first limiting structure 300 and the third limiting structure 300 as shown in FIG. 1. It is worth mentioning that in some embodiments of the combination of a plurality of limiting structures 300, the bearing table 304 needs to be offset from the setting position of the sliding plate groove 204 on the surface of the supporting plate 203.

It is worth mentioning that, in the embodiments of the present application, in order to further improve the shielding effect of the shielding device on the main control member 500, the shielding device also comprises a shielding plate (not shown), the shielding plate is connected to the end of the shielding case 401, forming a closed cavity with the shielding case 401, and the main control member 500 is accommodated in the closed cavity. For example, the supporting platform 200 forms a shielding plate to enhance the magnetic shielding effect of the closed cavity.

With respect to the shielding device provided in the embodiment of the present application, a magnetic control capsule endoscope system (not shown) is provided in a second embodiment of the present application. The magnetic control capsule endoscope system comprises: the shielding device described in the above embodiment, a strongly magnetic main control member 500, a support 600 for supporting the main control member 500, and a fixture platform 100 for installing the support 600. The support 600 supports the main control member 500 for movement, and the shielding case 401 of the shielding device is used to shield the main control member 500 supported by the support 600, thereby preventing the main control member 500 from adversely affecting the surrounding magnetic-sensitive components. The magnetic control capsule endoscope system can switch the working state and the shielding state of the main control member 500.

It should be noted that, relationship terms as described herein such as first and second are used only to distinguish one entity or operation from another, but do not necessarily require or imply any such actual relationship or sequence between these entities or operations. Moreover, the terms "include", "comprise" or any other variant thereof are intended to cover non-exclusive inclusion, so that a process, method, article or device that includes a series of elements includes not only those elements but also other elements that are not explicitly listed or further includes the elements inherent to such process, method, article or device. Without further limitation, the element limited by the statement "comprises a . . . " does not preclude the existence of another identical element in the process, method, article or equipment that includes said element.

In accordance with embodiments of the present application as described above, these embodiments do not elaborate all details, and do not limit the application to said embodiments. Obviously, a plurality of modifications and changes can be made based on the above description. These embodiments have been selected and specifically described in this specification in order to better explain the principles and practical applications of the present application, so those skilled in the art can make good use of the present application and the modify based on the present application. The present application is limited only by the claims and their full scope and equivalents.

The invention claimed is:

1. A shielding device for shielding a ferromagnetic main control member supported by a support, comprising:
   a shielding case and a lifting mechanism, wherein the shielding case is connected to the lifting mechanism, and the lifting mechanism drives the shielding case to slide in a direction close to or away from the main control member;
   the shielding device further comprises a limiting structure, wherein the limiting structure is in contact with the main control member and/or the support, for restricting the movement of the main control member supported by the support.

2. The shielding device of claim 1, wherein the lifting mechanism comprises:
   a sliding support member;
   a sliding assembly, wherein the sliding assembly is fixedly connected to the shielding case and sliding along the sliding support member to drive the shielding case away from the main control member or enclose the main control member; and,
   a lifter, and a push rod for controlling the lifting and lowering of the shielding case by the lifter, wherein the push rod is connected to the shielding case to drive the shielding case to slide in the direction close to or away from the main control member.

3. The shielding device of claim 1, wherein the limiting structure comprises a supporting structure and a limiting member, wherein the limiting member is disposed at one end of the supporting structure near the main control member, and the limiting member is in contact with the main control member and/or the support under the support of the supporting structure and restricts the movement of the main control member.

4. The shielding device of claim 3, wherein the support is configured as a robotic arm, the supporting structure comprises a support frame, and the limiting member comprises a clamping member;
   the support frame is used to support the clamping member,
   the clamping member is fixed to the top of the support frame, and the clamping member is used to clamp the robotic arm to restrict the movement of the main control member.

5. The shielding device of claim 4, wherein the robotic arm comprises a first sub-arm and a second sub-arm rotatably connected, and the clamping member is configured as a groove;

the groove is used to embed the second sub-arm, and when the second sub-arm is embedded in the groove, the projections of the first sub-arm and the second sub-arm on the target plane are two straight lines with a fixed angle, wherein the target plane is the plane where the bottom of the groove is located;

and, during the rotation of the first sub-arm, only one position in which the second sub-arm is embedded into the groove.

6. The shielding device of claim 4, wherein the limiting structure further comprises a groove lifter, the groove lifter is used to control the lifting and lowering of the support frame so that the clamping member is raised and lowered by the groove lifter and the support frame.

7. The shielding device of claim 3, wherein the supporting structure comprises a supporting platform, the shielding case is arranged on the outside of the supporting platform, and the sliding support member is arranged on one side of the supporting platform;

the supporting platform comprises a fixing frame and a supporting plate, wherein the supporting plate is installed through the fixing frame, and the supporting plate is used to support the main control member;

the limiting member is disposed on the edge of the side of the supporting plate facing the main control member to restrict the movement of the main control member.

8. The shielding device of claim 7, wherein the limiting member comprises a protective sliding plate, the protective sliding plate is disposed at the edge of the surface of the supporting plate, and the side of the protective sliding plate facing the shielding case in an upright state is a smooth surface.

9. The shielding device of claim 8, wherein a sliding plate groove is provided on the surface of the supporting plate;

the protective sliding plate is installed in the groove of the sliding plate groove in a manner that rotates around its bottom, wherein the protective sliding plate is disposed upright in the sliding plate groove in a magnetic shielding state, and embedded in the sliding plate groove in a non-magnetic shielding state;

the supporting platform further comprises a locking structure, the locking structure comprising a locking button, and the locking structure is used to control the protective sliding plate to be in a locked state or an unlocked state in the sliding plate groove through the locking button.

10. The shielding device of claim 7, wherein, the main control member comprises a magnet, the magnet is enclosed through the main control member shell;

the limiting member comprises a bearing table, the bearing table is fixed on the surface of the supporting platform for bearing the main control member;

the tabletop of the bearing table and the end of the main control member shell near the bearing table are shaped to be embedded in each other.

11. A magnetic control capsule endoscope system, comprising:

the shielding device, the ferromagnetic main control member, and the support for supporting the main control member of claim 1, and a fixture platform for installing the support;

wherein the support supports the main control member for movement, and the shielding case of the shielding device is used to shield the main control member supported by the support.

* * * * *